United States Patent [19]

Yanik

[11] Patent Number: 5,752,951
[45] Date of Patent: May 19, 1998

[54] SHIELDED MONOPOLAR ELECTROSURGICAL APPARATUS

[76] Inventor: Gary W. Yanik, 8718 Man O'War Rd., Palm Beach Gardens, Fla. 33418

[21] Appl. No.: 678,406

[22] Filed: Jul. 2, 1996

[51] Int. Cl.$^6$ ............................................. A61B 17/36
[52] U.S. Cl. ........................... 606/34; 606/35; 606/41; 606/46; 606/52
[58] Field of Search ............... 606/32–35, 39–42, 606/45–52, 205–208

[56] References Cited

U.S. PATENT DOCUMENTS

| | | | |
|---|---|---|---|
| 4,184,492 | 1/1980 | Meinke et al. | 606/46 |
| 4,200,105 | 4/1980 | Gonser | 606/35 |
| 4,819,633 | 4/1989 | Bauer et al. | 606/52 |
| 5,312,401 | 5/1994 | Newton et al. | 606/46 |
| 5,618,304 | 4/1997 | Hart et al. | 606/205 |

*Primary Examiner*—Michael Peffley
*Attorney, Agent, or Firm*—McHale & Slavin

[57] ABSTRACT

The instant invention is a shielded monopolar electrosurgical instrument for use in laparoscopic and the like surgical procedures. The instrument consists of a rigid outer metallic shield which operates as a conductive coaxial shield and is connected to a patient return electrode of an electrosurgical generator. The use of a coaxial shield coupled to the patient return electrode on the outer surface of the instrument eliminates the need for an outer insulative coating. The shield houses a conductive wire positioned through the center of the shield which is coupled to the active lead from the electrosurgical generator. Between the wire and the shield is placed an insulating sleeve. The tip of the instrument is interchangeable and the instrument may be used in conjunction with a form fitting handle providing the surgeon with finger holes in order to apply pressure to the instrument for operation of grasping items when such a tip is employed.

12 Claims, 3 Drawing Sheets

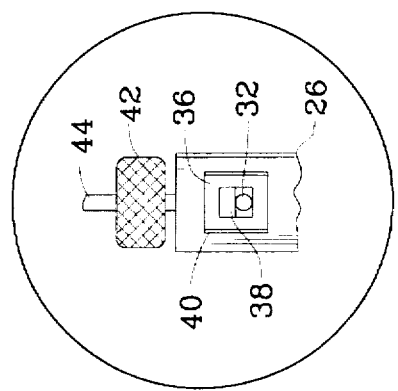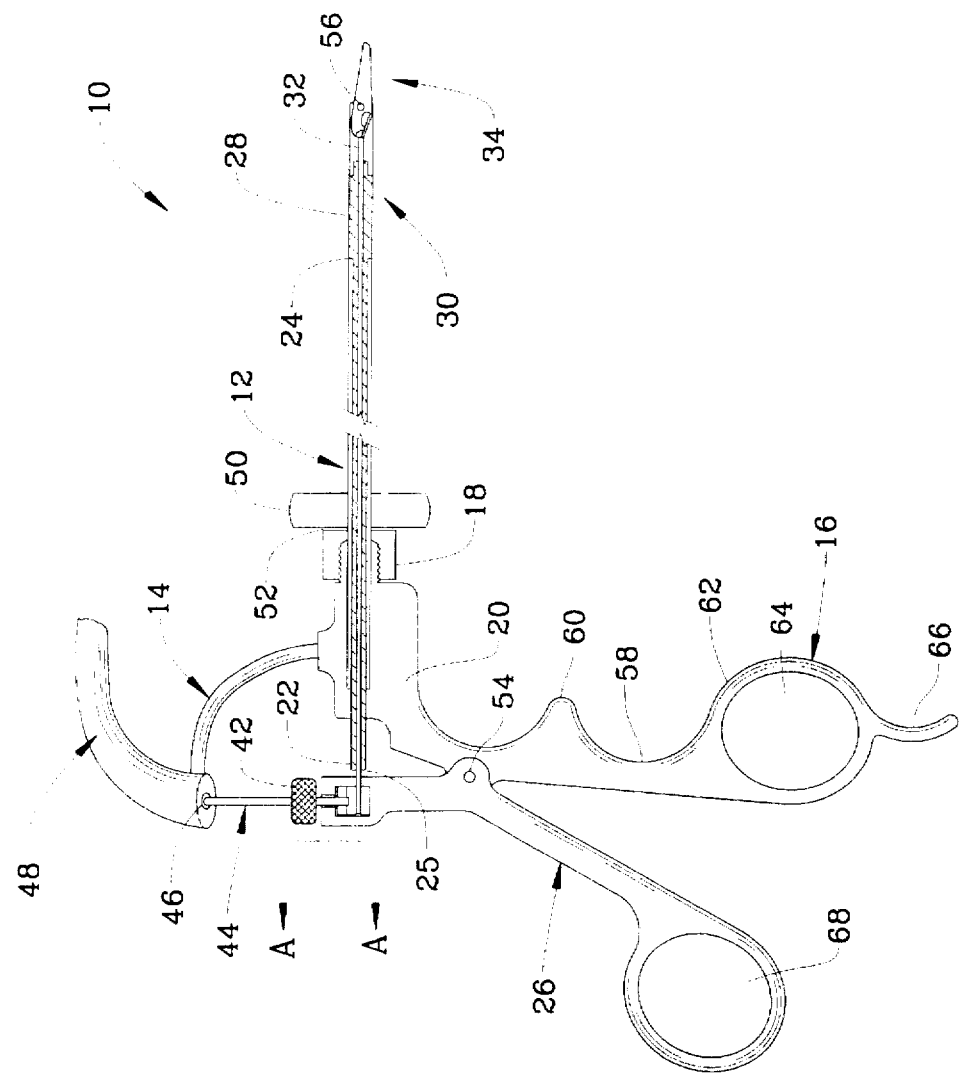

SHIELDED MONOPOLAR ELECTROSURGICAL APPARATUS

FIELD OF THE INVENTION

This invention relates generally to electrosurgical instruments and more particularly to a monopolar shielded instrument for use in procedures such as laparoscopic, pelviscopic, arthroscopic, thoracoscopic and the like.

BACKGROUND OF THE INVENTION

Modern surgical procedures, such as laparoscopic surgery, have revolutionized the practice of medicine eliminating the need for large abdominal incisions as previously required in order to perform a number of surgical operations. For instance, a method of laparoscopic cholecystectomy has eliminated the need for abdominal incisions as previously required allowing gall bladder surgery to be performed on a near outpatient basis requiring only small incisions be made in the umbilicus, lower and upper abdomen. In such an operation a trocar is inserted into an umbilicus incision with a removable stylet to provide for insertion of a laparoscope allowing viewing on a video screen. Additional incisions are made for insertion of cannulas used to permit surgical instruments to be inserted therethrough.

The surgeon may utilize any number of various type instruments having specialty shaped tips. A spatula shaped spoon is ideal for conforming to a gall bladder bed and bluntly dissecting the gall bladder from the liver. Another popular instrument is a rigid wire attached to the end of the laparoscopic instrument formed in the shaped of a J or L hook. Tips of the device may further include needle shapes, scissors, and graspers all of which serve various known functions including irrigation, cutting, and suction. Insertion is made by use of a trocar sheath or cannula which is used to provide a conduit through the skin into the peritoneal cavity. Unique to these instruments is the ability to apply energy through the surgical tool as supplied by an electrosurgical generator. The tool may then assist in cutting coagulation and cauterizing by heating of the contacted tissues.

A problem with prior art electrosurgical devices arises if the insulation on the instrument is damaged. Damage may consist of microscopic cracks in the insulation which are difficult for the human eye to detect. Prior art devices require the active electrode to be placed through a trocar sheath wherein the insulation can be damaged by friction as the sheath engages the sidewalls of the insulation. During a surgical procedure the possibility of active current passing through the damaged area of the insulation becomes a distinct possibility wherein the resulting arc may pass through a patient's tissue causing undetectable damage resulting in conditions such as peritonitis. This is a latent condition and may not be detected for days after the surgery has been performed. The laparoscopic procedure limits the surgeon's view to the tip of the scope with a field of view typically less than three centimeters in diameter.

FIG. 1 illustrates a prior art electrosurgical instrument having a trocar sheath or cannula 110 used as a conduit through a patient's skin for insertion of the surgical instrument. The surgical instrument in this embodiment is illustrated by an active electrode 112 having a layer of insulation coating 114 which includes an electrode 116 with a electrode 116 shown here as a hook shaped tip. The problem arises should the insulation 114 be damaged thereby allowing an arcing condition to occur wherein current may pass from the probe tip 118 through the insulation 114 and contact the patient's body which is at a separate potential due to the connection to the body from the electrosurgical generator of a patient potential pad.

One attempt to address this problem is disclosed in U.S. Pat. No. 5,312,401 by use of a thin coaxial shield placed over the outer insulation for use as a sensor to detect the current between the shield and the patient return electrode of the electrosurgical generator. Provisions are made for turning off the generator should an abnormal current be detected. In this embodiment an electrical terminal is connected to a shield and reference potential wherein current flows through the shield from an active probe to a reference potential for disabling the generator. The purpose of the insulation on the outer surface is stated to insure that the shield is insulated from the trocar sheath and to prevent the shield from becoming an unintentional return electrode. Should insulation on the active electrode be breached, current that will pass through the breach will be detected by a monitor circuit responsive to shield current which will in turn deactivate the electrosurgical generator. The problem with the patented device is the disabling effect that the device has upon the electrical surgical generator thus providing a remedy to a failed electrode using a complex current monitoring system but fails to address the primary cause for an insulation breach and furthermore does not provide any means for the surgeon to locate the location of the insulation failure so that the surgeon can address the situation and continue with the operation.

Referring to FIG. 2, the aforementioned invention is illustrated having a probe assembly set forth in a trocar sheath or cannula 130 having an active electro probe 132. In this embodiment a cavity is provided 134 for removal of irrigation fluids by suction. When the active probe 132 is inserted, the shield 136 and tubular shield assembly 138 are protected from arcing by use of a shield monitor system that determines abnormal current flow. The active electrode 132 is coupled to an electrical surgical generator by an active lead 140. A patient return electrode is also connected to the shield monitory circuit showing the potential between dual connector leads 142 to inner insulation area 144. A primary disadvantage of the instant disclosure is the complicated mechanism necessary to make the unit operational as well as the maintenance of the insulation on the outer side of the active electrode which presents a problem should the electrode insulation be damaged thus leading to the aforementioned burn problems which can be prevented by the disclosure which has a shield monitor circuitry which will shut off the electrical surgical generator. While the ability to shut down the electrical surgical generator should an arc occur is deemed an improvement to the prior art, it does not remedy the situation which requires addressing the problem of the arc in the first place.

Still another problem with the prior art is the electro coupling between the electrode and the trocar sheath. In such a situation current from the active electrode can be carried to the trocar sheath and transmitted through the patient's body. This may result in a mild form of isolated electrification which can damage an organ through burns and the like destruction of cells.

Thus, what is needed in the art is an electrosurgical tool that eliminates the need for external insulation thereby reducing the possibility of wayward current flow.

SUMMARY OF THE INVENTION

The instant invention sets forth a monopolar electrosurgical instrument defined by a rigid metallic tube which provides mechanical rigidity and serves as a conductive coaxial shield. The tube is coupled to the patient return electrode of an electrosurgical generator, thus eliminating the need for an outer insulative coating. In this manner the shield operates as a conductive housing maintaining an equal potential between the patient's body and the conductive shield.

Within the shield is placed a stainless steel or the like conductive wire which is electrically connected to the electrical surgical generator at one end with an interchangeable tip which serves as the active electrode at the opposite end. An insulating sleeve such as PEEK tubing or polyeretherketone is positioned between the wire and the shield in a centrally disposed position as well as providing a barrier insulator between the active electrode and the patient electrode.

The use of the conductive coaxial shield prevents mishaps such as destruction of the insulation found on prior art devices and further provides the ability to maintain insulation within an enclosed environment, namely the inner surface of the rigid shield. For this reason, the sleeve is deemed impervious to disruption as the only component that would come in contact with the sleeve is the wire electrode. The wire electrode is a smooth circular diameter creating negligible wear on the sleeve and further providing the benefit that should arcing take place it will be contained within the shield thus preventing any burns or related injury to the patient. The sleeve can be made integral with the shield, a coating to the wire, or as a replaceable sleeve.

In operation the outer conducting shield can be securely mounted to a hand held piece maintained at the same potential as the patient by connecting to the patient return electrode. A second insulated handle has an outer portion of the handle coupled to the hand held piece providing the concurrent potential through direct metal contact. The second handle includes an insulated interactive lead which couples to the active electrode wire.

Thus, an objective of the instant invention is to disclose a method of insulating an electrosurgical instrument by provision of an insulating material within a hollow shield and providing an outer conducting shield which is coupled to a patient return electrode of an electrosurgical generator.

Still another objective of the instant invention is to provide an surgical tip coupled to active electrode having a tip body fabricated from a non conductive material.

Another objective of the instant invention is to provide a electrosurgical instrument that accommodates various tip shapes for coagulating and cauterizing.

Still another objective of the instant invention is to contain an active electrode and protect the insulating sleeve within a rigid metal tube providing longevity in adverse conditions.

Still another objective of the instant invention is to disclose the use of a handle mechanism having a separate conductive shield connection and active electrode connection providing clear distinguishing connection points.

In accordance with these and other objectives which will become apparent hereafter, the instant invention will now be described with particular reference to the accompanying drawings.

BRIEF DESCRIPTION OF THE DRAWINGS

FIG. 3 a partial cross-sectional side view of the electrosurgical instrument of the instant invention;

FIG. 3A is a partial cross-sectional end view taken along lines A—A of FIG. 3;

DETAILED DESCRIPTION OF THE PREFERRED EMBODIMENT

Figure 1:
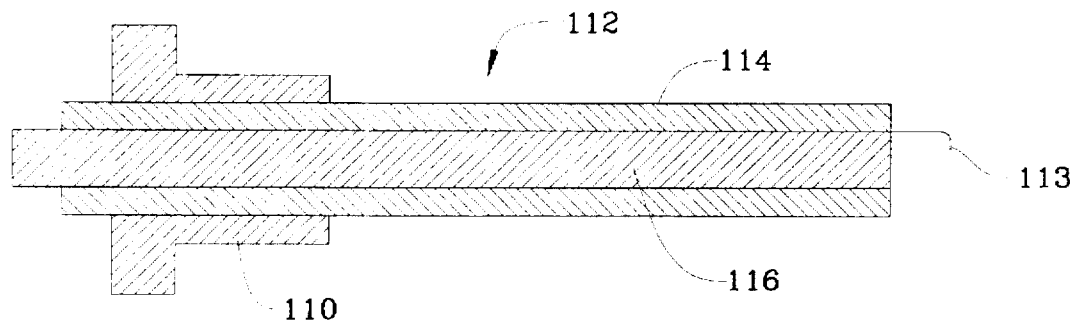
FIG. 1 a cross-sectional side view of a prior art electrosurgical device.
Figure 2:
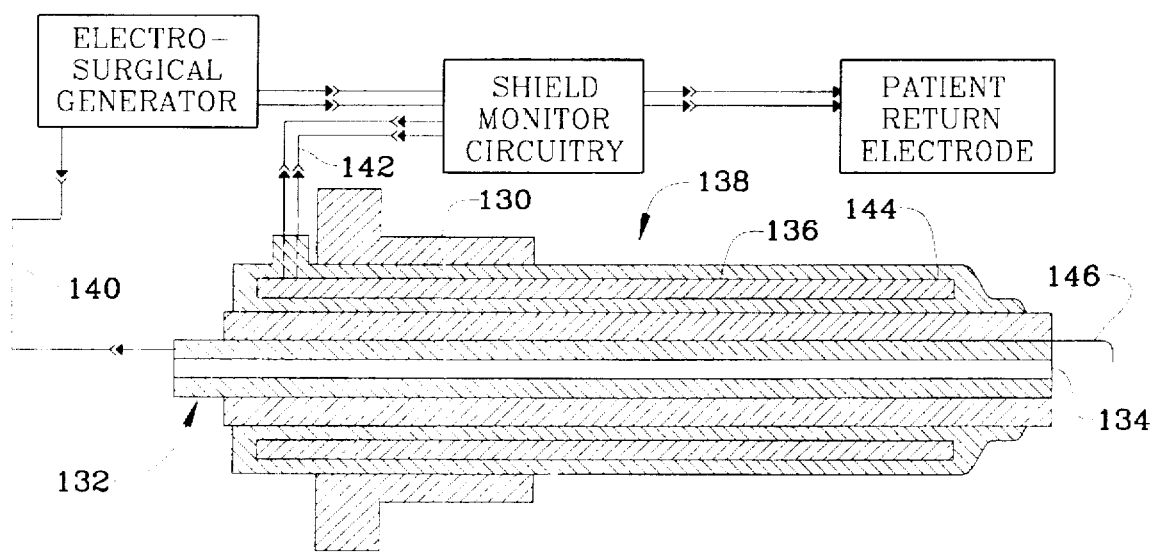
FIG. 2 a cross-sectional side view of another prior art electro surgical device.

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Referring to FIG. 3 illustrated is the instant invention 10 positioned within a hand held laparoscopic instrument. The device consists of a rigid outer metallic tube 12 having a longitudinal length. The rigid tube 12 operates as a conductive coaxial shield and is coupled to a patient return electrode 14 by securement to conductive handle 16 by frictional engagement of locking head 18 which threadingly engages to a shield support housing 20 located along an upper portion of the conducting handle 16. Insulating sleeve 22 is positioned within the shield 12 extending from a first point 25 juxtapositioned to insulating handle 26 to a distal end 24. The insulating sleeve 22 is manufactured from polyetheretherketone, PEEK tubing, ceramic, or like non-conductive material.

The conductive coaxial shield 12 is elongated with an exposed portion 28 which supports tip housing 30. The tip housing 30 includes a portion of the tip and may use threads available for engaging the inner surface of shield 12 or having a friction fit. Tip housing 30 may be fitted with any shaped device commonly used with electrosurgical instruments such as a spatula, L-hook, J-hook, scissors, cutting tip, squeezers, and so forth and having a body fabricated from a non conductive material. Interchangeability of the tool is made in accordance with the particular operating procedure. An inner steel wire 32 operates as an active electrode and is coupled directly to tip 34 providing a direct connection to the active lead of an electrosurgical generator.

The steel wire engages the insulating handle 26 by use of threaded attachment nut 42 having a centrally disposed electrode connection 44 which couples to the center conductive connection 46 of coaxial cable 48. The outer portion of the coaxial cable 48 is maintained at patient body potential as provided by direct coupling to electrode 14. As shown in FIG. 3A the wire 32 is electrically secured to the electrode 44 by vice clamp 36 which pinches the wire 32 to the inner surface of float vice box 38 providing an isolation area to handle 36. Spacing 40 allows flotation of the box 38 or in an alternative embodiment provides the isolation area by free air space. Rotation knob 50 is formed permanently to shield 12 having frictional reduction spacer washer 52 positioned between the rotation knob 50 and coupling nut 18.

In this embodiment, once the coupling nut 18 is secured to the body 20, rotation knob 50 allows ease of rotation of tube shield 12 and tip housing 34 by a direct correlation while turning rotation knob 50. If the surgical instrument is used as a tweezers or pliers, tip 40 can open as provided by biasing point 54 which allows movement of the steel wire 38 along the longitudinal length of the sleeve 22 for rotation of the tip 40 into a particular position as provided by biasing point 56. It should be noted that steel wire 38 provides a constant electrical connection between the active electrode of the electrosurgical generator through coaxial cable 48 by coupling to electrode 44.

Conducting handle 16 provides for ease of operation by use of an index finger curvature 58 having a raised lip 60 that works in conjunction with the outer surface 62 of finger hole 64 for positioning the index and middle finger in position. Tail hook 66 allows the surgeon to rest the third finger, all of which allows sufficient strength in pulling finger hole 68 of insulating handle 26 into a closed position providing a strong clamping ability despite fluids that may coat the handles.

Figure 4:
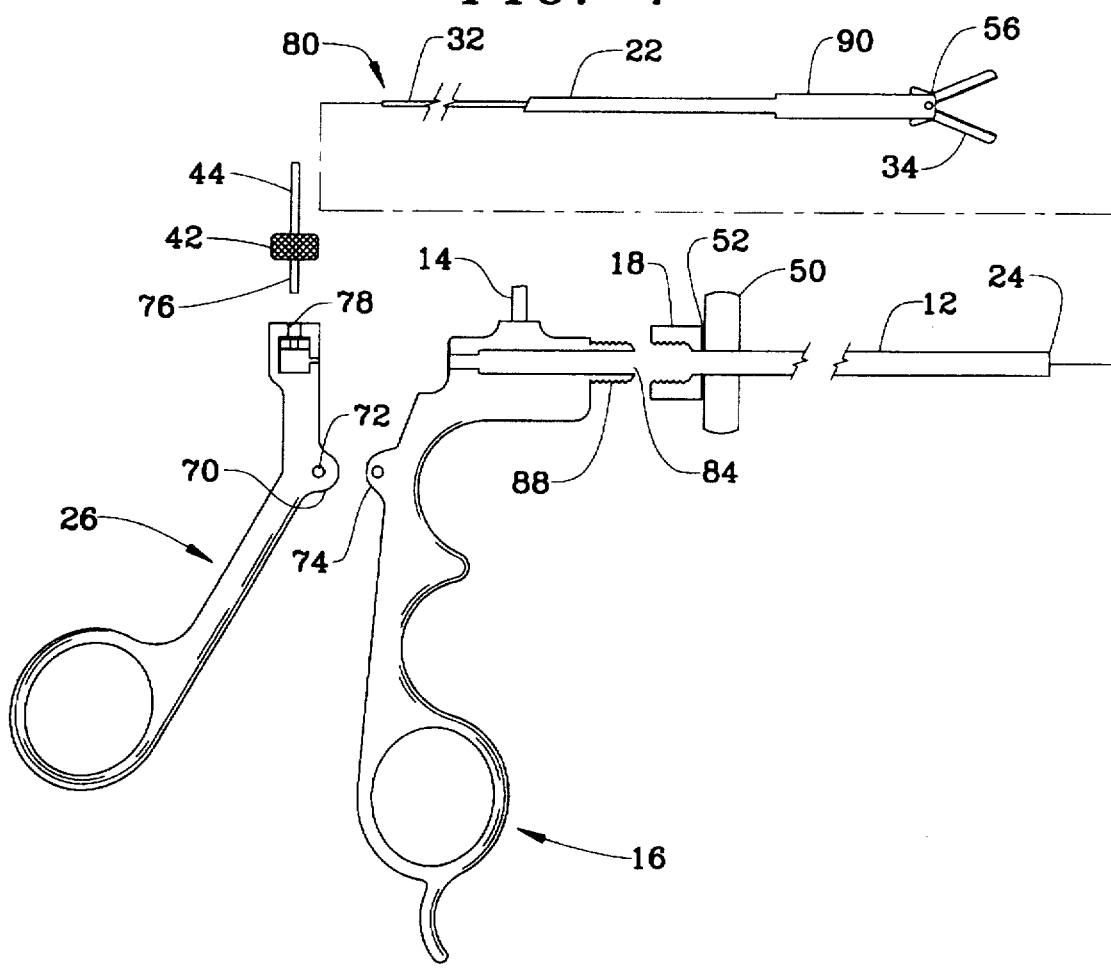
FIG. 4 is an exploded view of FIG. 3.

Now referring to FIG. 4, shown is an exploded view of the instant invention according to FIG. 3 having conducting handle 16 separated from insulating handle 26 illustrating pivot point 70 having an aperture 72 available for insertion of a pivot bolt, not shown, in combination with boss 74 of conducting handle 16 allowing the handles to pivot accordingly. The insulating handle 26 shows active lead 44 and tightening nut 42 having threaded screw base 76 operatively associated with float vice box 38 wherein the end of threaded screw 76 engages end 80 of wire 32 which allows a positive contact of the active lead 44 at all times whether the handles have been pivoted apart as well as allowing the wire 32 to rotate. Interactive lead 44 engages end 80 and is isolated from insulating handle 26 which prevents arcing of the interactive lead to any uninsulated portion of the instrument that is coupled to the patient return electrode.

The conducting handle 16 includes the insulating sleeve 22 which extends outward from the handle through chamber 84 so as to insulate the chamber from electrical connection to the outer conducting shield patient return electrode 86. The outer surface of the handle 16 includes a portion 88 which is threaded for receipt of the shield 12 by coupling nut 18 having internal threads for engagement of external threads. Frictional reduction spacer washer 52 allows tightening of the nut 18 without rotation of the shield 12. Upon coupling the shield 12, the turning of rotation knob 50 provides positioning of the cutting or conduction tip assembly 40 without frictionally engaging the surface of the nut 18.

The wire 32 electrically couples the first end 80 to distal end pivot point 56 which by way of illustration provides a tweezers. The distal end includes an enlarged external portion 90 which engages the open end 24 of the shield 12. As previously mentioned the wire 32 operates as the electrode and may be simply exchanged by unthreading active lead attachment nut 42 and sliding the sleeve 22 from shield 12 allowing a substitute electrode to be placed therein. Shield 12 need not be decoupled from handle 16 when use of a substitute active electrode having the same length is provided. Alternatively, the shield 12 can be decoupled from the handle and a shorter or longer shield and associated sleeve may be substituted in its place. Additionally, handles need not be utilized in all instances as the shield and electrode can be used in various embodiments as a pencil probe without defeating the intent of this invention which maintains an active inner electrode surrounded by an insulated sleeve for use with an outer shield which operates as a conducting shield coupled directly to the patient return electrode. It is noted that the conductive of said first handle and said second handle can be reversed.

Figure 5:
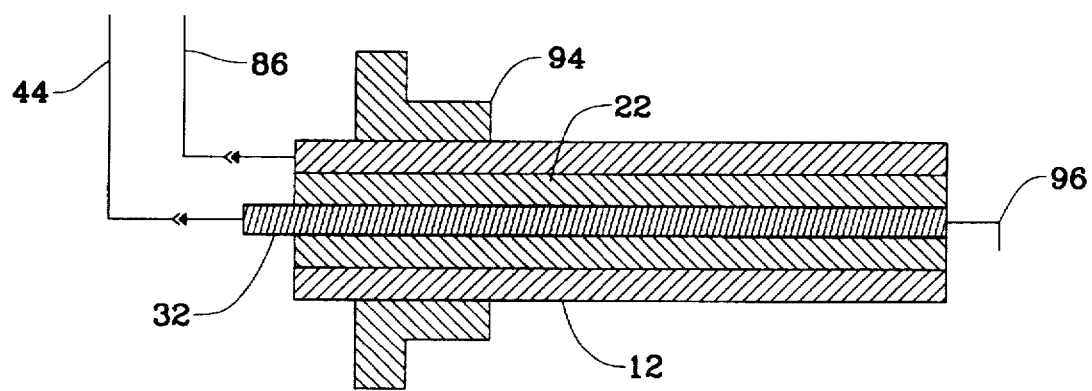
FIG. 5 a cross-section view of an illustrative laparoscopic apparatus in accordance with the present invention.

Now referring to FIG. 5, shown is a cross-sectional side view of the electrode 32 slidably insertable with an insulating sleeve 22 positioned within shield 12. As shown, the interactive lead electrode wire 32 is electrically coupled to the active lead 44 for connection to the electrosurgical generator. Similarly, outer conducting shield 12 is electrically coupled to patient return electrode 86 for coupling to the patient return electrode of the electrosurgical generator. In this illustration a hook 96 is placed at the end of the wire 32 and the instrument is shown within a trocar 94.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. An electrosurgical apparatus comprising: a hollow elongated housing constructed from a conductive material and defined by a proximal end and a distal end forming an interior chamber therebetween, said proximal end adapted for releasable coupling to a patient return electrode of an electrosurgical generator; an active electrode disposed within said chamber having a first end adapted for coupling to an active lead on said electrosurgical generator and a second end forming an exposed surgical tool for effecting at a tip of said tool an electrosurgical procedure; a means for electrically isolating said active electrode from said housing; a first handle electrically coupled to said housing and pivotally connected to a second insulated handle for support of said active electrode, said handles operatively associated with said active electrode for controlling longitudinal movement of said surgical tool; wherein said housing is adapted to be at the same potential as said patient return electrode when said housing is connected to the return electrode of the electrosurgical generator and whereby said active electrode is available for electrosurgery procedures and is electrically isolated from said housing.

2. The apparatus according to claim 1 including a means for isolating said second handle from said active electrode.

3. The apparatus according to claim 1 including a rotatable knob coupled to said housing means providing ease of rotation of said surgical tool.

4. An electrosurgical apparatus comprising:
a housing defined by a hollow elongated shield of conductive material defined by a proximal end and a distal end forming an interior chamber therebetween; a first handle electrically coupled to said housing and pivotally connected to a second insulated handle; an active electrode disposed within said interior chamber having a first end operatively associated with said first handle and adapted for coupling to an electrosurgical generator with a means for electrically isolating said first handle from said active electrode and a second end of said electrode adapted for coupling to a surgical tool for effecting an electrosurgical procedure at a tip, said second end of said active electrode having a tip body fabricated from a non-conductive material; a sleeve of non-conductive material for electrically isolating said active electrode from said housing, said sleeve positioned within said shield and extending from said proximal end to said distal end; a support formed from said second handle electrically coupled to said housing and pivotally connected to said first handle for support of said active electrode, said second handle having an electrode terminal for coupling to a patient return electrode on an electrosurgical generator and adapted to maintain said second handle and said housing at the same potential as said return electrode.

5. The apparatus according to claim 4, wherein said first handle includes a cavity for receipt of said first end of said active electrode, said cavity having a means for insulating said electrode from a body of said first handle.

6. The apparatus according to claim 5, wherein said first end of said active electrode is releasably secured in said cavity by an inner active lead having a lower end which electrically engages said first end of said active electrode and an upper end adapted to couple to a coaxial cable for connection to the electrosurgical generator.

7. The apparatus according to claim 4, wherein said housing means is releaseably coupled to said first handle including a means for allowing rotation of said housing means in relation to said first handle.

8. The apparatus according to claim 4, wherein said second end of said electrode threadingly engages said distal end of said housing means.

9. The apparatus according to claim 4, wherein said sleeve is constructed from non-conductive tubing.

10. The apparatus according to claim 4, wherein said sleeve is constructed from plastic tubing.

11. The apparatus according to claim 10, wherein said plastic is polyetheretherketone.

12. The apparatus according to claim 4, wherein the connections of the first handle and the second handle may be reversed.

* * * * *